(12) United States Patent
Hamer et al.

(10) Patent No.: US 10,398,602 B2
(45) Date of Patent: *Sep. 3, 2019

(54) EARPLUG WITH TIP CAVITY AND METHODS OF MANUFACTURING THE SAME

(71) Applicant: 3M INNOVATIVE PROPERTIES COMPANY, St. Paul, MN (US)

(72) Inventors: Jeffrey L. Hamer, Springville, IN (US); Kenneth F. Teeters, Zionsville, IN (US); Ravi Thomas, Avon, IN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 255 days.

This patent is subject to a terminal disclaimer.

(21) Appl. No.: 15/412,305

(22) Filed: Jan. 23, 2017

(65) Prior Publication Data

US 2017/0156933 A1 Jun. 8, 2017

Related U.S. Application Data

(63) Continuation of application No. 13/768,214, filed on Feb. 15, 2013, now Pat. No. 9,549,855.

(51) Int. Cl.
*A61F 11/08* (2006.01)
*B29C 44/12* (2006.01)
*B29K 101/10* (2006.01)
*B29K 101/12* (2006.01)
*B29L 31/00* (2006.01)

(52) U.S. Cl.
CPC .......... *A61F 11/08* (2013.01); *B29C 44/1271* (2013.01); *A61F 2011/085* (2013.01); *A61F 2210/0071* (2013.01); *A61F 2240/004* (2013.01); *A61F 2250/0014* (2013.01); *B29K 2101/10* (2013.01); *B29K 2101/12* (2013.01); *B29L 2031/768* (2013.01)

(58) Field of Classification Search
CPC combination set(s) only.
See application file for complete search history.

(56) References Cited

U.S. PATENT DOCUMENTS

| | | |
|---|---|---|
| 2,393,005 A | 4/1944 | Veneklasen |
| 2,538,339 A | 9/1949 | Thomas |
| 3,618,600 A | 11/1971 | Douglass |
| 3,736,929 A | 6/1973 | Mills |
| 4,052,754 A | 11/1977 | Homsy |
| 4,269,638 A | 5/1981 | Faranetta |
| 4,384,575 A | 5/1983 | Asker |

(Continued)

FOREIGN PATENT DOCUMENTS

| | | |
|---|---|---|
| CN | 2086136 | 10/1991 |
| DE | 2252392 | 5/1974 |

(Continued)

OTHER PUBLICATIONS

International Application No. PCT/US2014/013834 Search Report dated Apr. 14, 2014.

*Primary Examiner* — Ophelia A Hawthorne
(74) *Attorney, Agent, or Firm* — Katherine M. Scholz; Dena M. Ehrich

(57) ABSTRACT

Hearing protection devices, e.g., push-to-fit earplugs, having a tip cavity in the sound attenuating body and methods of manufacturing the hearing protection devices are described herein.

21 Claims, 5 Drawing Sheets

(56) References Cited

U.S. PATENT DOCUMENTS

| | | | |
|---|---|---|---|
| 4,540,063 A | 9/1985 | Ochi | |
| 4,564,009 A | 1/1986 | Brinkhoff | |
| 4,608,217 A | 8/1986 | Csiki | |
| 4,870,688 A | 9/1989 | Voroba | |
| 5,044,463 A | 9/1991 | Carr | |
| 5,153,387 A | 10/1992 | Zwislocki | |
| 5,203,352 A | 4/1993 | Gardner, Jr. | |
| 5,609,164 A | 3/1997 | Dyrud | |
| 5,742,692 A | 4/1998 | Garcia | |
| 5,799,658 A | 9/1998 | Falco | |
| 5,824,968 A | 10/1998 | Packard | |
| 5,904,143 A | 5/1999 | Magidson | |
| 6,484,726 B1 | 11/2002 | Remer | |
| 6,568,394 B2 | 5/2003 | Falco | |
| 6,820,717 B2 | 11/2004 | Fleming | |
| 6,981,504 B2 | 1/2006 | Jenkins, Jr. | |
| 7,022,272 B2 | 4/2006 | Brossman | |
| 7,600,604 B2 | 10/2009 | Babcock | |
| 7,697,706 B2 | 4/2010 | Doty | |
| 7,712,469 B2 | 5/2010 | Jenkins, Jr. | |
| 7,886,744 B2 | 2/2011 | Knauer | |
| 7,984,716 B2 | 7/2011 | Purcell | |
| 7,998,391 B1 | 8/2011 | Koo | |
| 8,061,472 B2 | 11/2011 | Tiemens | |
| 8,113,207 B2 | 2/2012 | Gehling | |
| 8,479,744 B2 | 7/2013 | Fleming | |
| 8,679,607 B2 | 3/2014 | Hamer | |
| 9,549,855 B2 * | 1/2017 | Hamer | A61F 11/08 |
| 2005/0056288 A1 | 3/2005 | Schreiber | |
| 2006/0049544 A1 | 3/2006 | Seitoh | |
| 2006/0175722 A1 | 8/2006 | Babcock | |
| 2006/0202375 A1 | 9/2006 | Jenkins, Jr. | |
| 2008/0276945 A1 | 11/2008 | Rosen | |
| 2009/0039555 A1 | 2/2009 | Jenkins, Jr. | |
| 2009/0071487 A1 | 3/2009 | Keady | |
| 2010/0307541 A1 | 12/2010 | Berg | |
| 2010/0307859 A1 | 12/2010 | Jayaraman | |
| 2012/0046607 A1 | 2/2012 | Syk | |

FOREIGN PATENT DOCUMENTS

| | | |
|---|---|---|
| EP | 0 108 728 | 5/1984 |
| FR | 2 230 336 | 12/1974 |
| GB | 1 398 401 | 6/1975 |
| JP | 56-16415 | 7/1979 |
| JP | 20021794 | 10/2002 |
| JP | 2009-172270 | 8/2009 |
| NL | 9401212 | 3/1996 |
| WO | WO 2011/061451 | 5/2011 |

* cited by examiner

EARPLUG WITH TIP CAVITY AND METHODS OF MANUFACTURING THE SAME

CROSS REFERENCE TO RELATED APPLICATIONS

This application is a continuation of U.S. application Ser. No. 13/768,214, filed Feb. 15, 2013, now U.S. Pat. No. 9,549,855, the entire content of which is incorporated herein by reference.

BACKGROUND

Hearing protection devices, e.g., push-to-fit earplugs, having a tip cavity in the sound attenuating body and methods of manufacturing the hearing protection devices are described herein.

The use of hearing protective and noise attenuating devices are well known, and various types of devices have been considered. Such devices include earplugs and semi-aural devices partially or completely constructed of foam or rubber materials that are inserted into, or placed over, the ear canal of a user to physically obstruct the passage of sound waves into the inner ear.

Compressible or "roll-down" type earplugs generally comprise a compressible, resilient body portion and may be made of suitable slow recovery foam materials. The earplug may be inserted into the ear canal of a user by first rolling it between fingers to compress the body portion, then pushing the body portion into the ear canal, and subsequently allowing the body portion to expand to fill the ear canal.

Push-to-fit type earplugs have also been considered, and may include a compressible attenuating portion and a stiff portion that extends from the attenuating portion. To insert a push-to-fit type earplug, the user grasps the stiff portion and pushes the attenuating portion into the ear canal with an appropriate level of force. The attenuating portion compresses as it is accommodated in the ear canal. Push-to-fit earplugs may allow the earplug to be quickly and easily inserted in an ear canal, and may promote hygiene by minimizing contact with the attenuating portion of the earplug prior to insertion.

Although push-to-fit earplugs exhibit desirable characteristics in various applications, they may be costly and may pose difficult manufacturing challenges.

SUMMARY

Hearing protection devices, e.g., push-to-fit earplugs, having a tip cavity in the sound attenuating body and methods of manufacturing the hearing protection devices are described herein.

The tip cavities in the earplugs as described herein may, in one or more embodiments, provide a volume into which the surrounding material of the sound attenuating body can collapse as the earplug is advanced into an ear canal and/or is resident therein. This feature may, in one or more embodiments, make insertion of the earplugs easier and/or improve comfort, particularly for users with smaller ear canals.

In addition to providing a volume for the material of the sound attenuating body to occupy, the end of a core located in the earplug may be recessed into the tip cavity, which may, in one or more embodiments, reduce the likelihood that a user will feel the end of the core as the sound attenuating body is inserted into and/or resident within an ear canal.

Although the end of the core is recessed within the tip cavity, it may, in one or more embodiments, extend into the tip cavity such that the end of the core is located above the bottom of the tip cavity as described herein.

The ends of the cores located within the tip cavities of earplugs as described herein may also, in one or more embodiments, have a non-planar surface that may also assist in reducing the likelihood that a user will feel the end of the core as the sound attenuating body is advanced into and/or resident within an ear canal. The ends of the cores may, in one or more embodiments, have a semi-spherical shape.

In one or more embodiments of the earplugs as described herein, flange cavities defining flanges at the bases of the sound attenuating bodies may be included. The flanges may be cantilevered from the sound attenuating body. Because the flanges are connected to the sound attenuating bodies at only one end, the flanges may deflect inwardly as the earplugs are advanced into an ear canal and/or are resident therein. Deflection of the flanges may, in one or more embodiments, improve insertion and/or comfort of the earplugs described herein.

In a first aspect, one or more embodiments of the earplugs as described herein may include a core comprising a first end, a second end, and a major outer surface, wherein a longitudinal axis extends between the first end and the second end; a sound attenuating body attached to the major outer surface of the core, the sound attenuating body comprising a tip and a base, wherein the tip of the sound attenuating body is located proximate the first end of the core and the base is located closer to the second end of the core than the first end of the core, and wherein the core extends through at least a portion of the sound attenuating body; and a tip cavity in the sound attenuating body. The tip cavity extends from the tip of the sound attenuating body towards a bottom nearest to the base of the sound attenuating body, wherein the tip cavity comprises a tip cavity cross-sectional area that is greater than a core cross-sectional area, wherein the tip cavity cross-sectional area is measured in a first plane located at the first end of the core and transverse to the longitudinal axis, wherein the core cross-sectional area is measured in a second plane transverse to the longitudinal axis, wherein the second plane passes through the sound attenuating body below the bottom of the tip cavity and above the base of the sound attenuating body.

In one or more embodiments of the earplugs as described herein, the tip cavity cross-sectional area is 1.5 or more times the core cross-sectional area.

In one or more embodiments of the earplugs as described herein, at least a portion of the first end of the core is exposed at the bottom of the tip cavity.

In one or more embodiments of the earplugs as described herein, the first end of the core is located above the bottom of the tip cavity.

In one or more embodiments of the earplugs as described herein, the core comprises a head located in the tip cavity, wherein the first end of the core is located on the head, and wherein at least a portion of the head comprises a head cross-sectional area that is greater than the core cross-sectional area, wherein the head cross-sectional area is measured in a plane orthogonal to the longitudinal axis and located above the bottom of the tip cavity and below the first end of the core.

In one or more embodiments of the earplugs as described herein, the core comprises a head located in the tip cavity, and wherein the head comprises a non-planar upper surface facing away from the bottom of the tip cavity.

In one or more embodiments of the earplugs as described herein, the core comprises a head located in the tip cavity, and wherein the head comprises a semispherical upper surface facing away from the bottom of the tip cavity shape.

In one or more embodiments of the earplugs as described herein, the sound attenuating body comprises a tip volume that is defined as a volume of the second material of the sound attenuating body located between the tip and the first plane, and wherein the tip cavity comprises a tip cavity volume that is defined as the volume of the tip cavity between the first plane and a tip cavity opening plane that is defined as the plane furthest from the first plane that is transverse to the longitudinal axis and that intersects with the sound attenuating body around the entire perimeter of the tip cavity, and further wherein the tip cavity volume is 10% or more of the tip volume. In one or more embodiments, the tip cavity volume is 20% or more of the tip volume.

In one or more embodiments of the earplugs as described herein, the sound attenuating body comprises a foamed material that comprises a plurality of gas cells that comprise a mean cell volume, and wherein the tip cavity volume is 20000 or more times the mean cell volume.

In one or more embodiments of the earplugs as described herein, the sound attenuating body comprises a flange cavity extending from the base of the sound attenuating body towards the tip of the sound attenuating body, wherein the sound attenuating body comprises a cantilevered flange formed around the flange cavity and extending from the base of the sound attenuating body towards the tip of the sound attenuating body.

In one or more embodiments of the earplugs as described herein, the sound attenuating body is thermally bonded to at least a portion of the outer major surface of the core.

In one or more embodiments of the earplugs as described herein, an adhesive is not present between the outer major surface of the core and the sound attenuating body.

In one or more embodiments of the earplugs as described herein, the core is constructed of a first material and the sound attenuating body is constructed of a second material, wherein the first material is different than the second material. In one or more embodiments, the first material comprises a thermoplastic. In one or more embodiments, the second material comprises a thermoset polymer.

In one or more embodiments of the earplugs as described herein, the core comprises a cross-section that is uniform at any location between the bottom of the tip cavity and the second end of the core.

In one or more embodiments of the earplugs as described herein, the core comprises a channel extending through the core from the first end to the second end.

In a second aspect, one or more embodiments of the earplugs as described herein may include a core comprising a first end, a second end, and a major outer surface, wherein a longitudinal axis extends between the first end and the second end; a sound attenuating body attached to the major outer surface of the core, the sound attenuating body comprising a tip and a base, wherein the tip of the sound attenuating body is located proximate the first end of the core and the base is located closer to the second end of the core, and wherein the core extends through at least a portion of the sound attenuating body; and a tip cavity in the sound attenuating body. The tip cavity extends from the tip of the sound attenuating body towards a bottom nearest to the base of the sound attenuating body, and wherein the tip cavity comprises a tip cavity cross-sectional area that is 1.5 times or more of a core cross-sectional area, wherein the tip cavity cross-sectional area is measured in a first plane located at the first end of the core and transverse to the longitudinal axis, and wherein the core cross-sectional area is measured in a second plane transverse to the longitudinal axis, wherein the second plane passes through the sound attenuating body below the bottom of the tip cavity and above the base of the sound attenuating body. The core comprises a head located in the tip cavity, wherein the first end of the core is located on the head and above the bottom surface of the tip cavity, and wherein at least a portion of the head comprises a head cross-sectional area that is greater than the core cross-sectional area, wherein the head cross-sectional area is measured in a plane that is orthogonal to the longitudinal axis and located above the bottom of the tip cavity and below the first end of the core. The core is made of a first material and the sound attenuating body is made of a second material, wherein the first material and the second material are different.

In one or more embodiments of the earplugs as described herein, the sound attenuating body comprises a flange cavity extending from the base of the sound attenuating body towards the tip of the sound attenuating body, wherein the sound attenuating body comprises a cantilevered flange formed around the flange cavity and extending from the base of the sound attenuating body towards the tip of the sound attenuating body.

In a third aspect, one or more embodiments of methods of making an earplug as described herein may include: covering at least a portion of a major outer surface of a core that comprises a first material with a second material that comprises an unactivated foaming agent, wherein the core comprises a first end, a second end, and a major outer surface, wherein a longitudinal axis extends between the first end and the second end; inserting the first end of the core and at least a portion of the second material into a mold cavity; and activating the unactivated foaming agent in the mold cavity to form a sound attenuating body in the mold cavity that is attached to the major outer surface of the core. The sound attenuating body comprises: a tip and a base, wherein the tip of the sound attenuating body is located proximate the first end of the core and the base is located closer to the second end of the core than the first end of the core; and a tip cavity in the sound attenuating body, wherein the tip cavity extends from the tip of the sound attenuating body towards a bottom nearest to the base of the sound attenuating body, and wherein the tip cavity comprises a tip cavity cross-sectional area that is greater than a core cross-sectional area, wherein the tip cavity cross-sectional area is measured in a first plane located at the first end of the core and transverse to the longitudinal axis, wherein the core cross-sectional area is measured in a second plane transverse to the longitudinal axis, wherein the second plane passes through the sound attenuating body below the bottom of the tip cavity and above the base of the sound attenuating body.

In one or more embodiments, the methods described herein may include deforming the first end of the core in the mold cavity.

In one or more embodiments, the methods described herein may include a boss extending into the mold cavity, wherein the boss is positioned to contact the first end of the core when the first end of the core is inserted into the mold cavity. In one or more embodiments, the method may include deforming the first end of the core using the boss.

Glossary

"Mold" means a hollow form that may or may not impart a shape on a component placed in the hollow form.

"Thermally bonded" means a state in which molecules of two materials or surfaces have diffused into the material or surface of the other when in a molten phase such that a bond is formed. Chemical bonding is absent or does not provide the primary source of bonding between thermally bonded materials or surfaces.

"Thermoplastic" means a polymer that can be repeatably heated and re-shaped and will retain its shape upon cooling.

"Thermoset" means a polymer that may be irreversibly cured.

"Unactivated" when referring to a foaming agent means that the foaming agent can be further activated to facilitate the formation of gas or cells in a material.

The words "preferred" and "preferably" refer to embodiments described herein that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the terms "comprises" and variations thereof do not have a limiting meaning where these terms appear in the accompanying description. Moreover, "a," "an," "the," "at least one," and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

The above summary is not intended to describe each embodiment or every implementation of the earplugs and methods of manufacturing earplugs as described herein. Rather, a more complete understanding of the invention will become apparent and appreciated by reference to the following Description of Illustrative Embodiments and claims in view of the accompanying figures of the drawing.

BRIEF DESCRIPTION OF THE DRAWINGS

FIGS. 3-6 are cross-sectional views of alternative illustrative embodiments of push-to-fit earplugs as described herein.

DESCRIPTION OF ILLUSTRATIVE EMBODIMENTS

Figure 1:
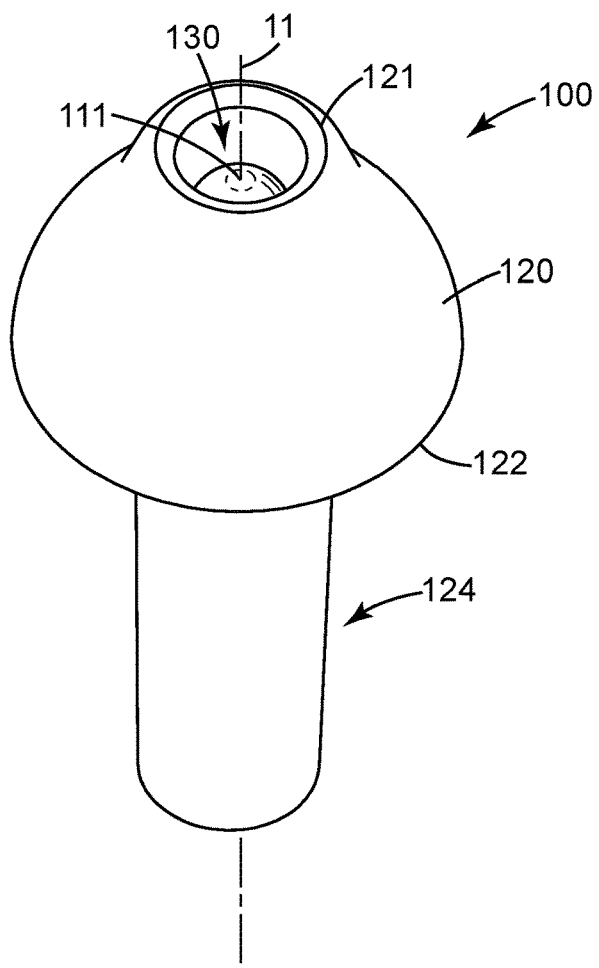
FIG. 1 is a perspective view of one illustrative embodiment of a push-to-fit earplug including a tip cavity as described herein.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

Earplugs that provide hearing protection for a user and methods of making earplugs are described herein. In one or more embodiments, the earplugs as described herein include a relatively stiff core covered, directly or indirectly, by a relatively soft outer layer. The outer layer forms a compressible sound attenuating body that may be inserted into the ear canal of a user. The earplugs described herein also include, in one or more embodiments, a stem portion that may include the relatively soft outer layer over the core, with the stem portion used to handle the earplug during, e.g., insertion and removal. In one or more embodiments, the earplugs as described herein may be inserted into an ear canal without first requiring that the sound attenuating body be compressed or "rolled down."

One or more embodiments of methods of making earplugs are also described herein. In one or more embodiments, the methods may reduce the difficulty and/or the cost of manufacturing earplugs as described herein. The methods may, in one or more embodiments, include covering a substrate, such as a core, with an outer layer that includes an unactivated foaming agent, and activating the foaming agent such that at least a portion of the outer layer expands into a desired shape.

Figure 2:
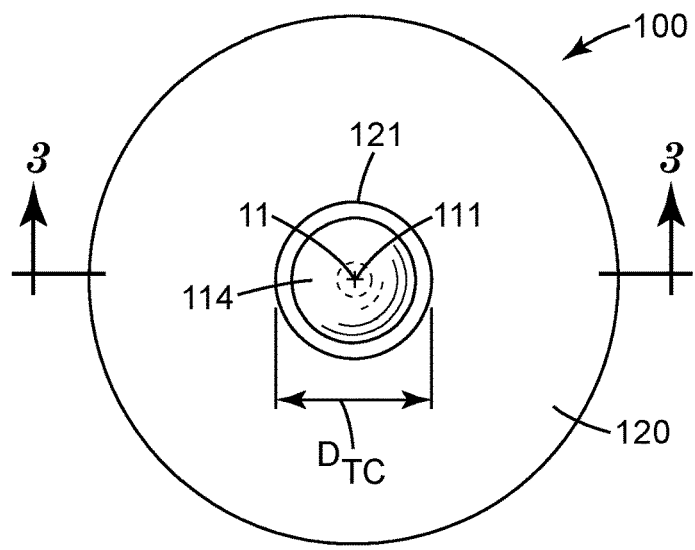
FIG. 2 is an end view of the earplug of FIG. 1 taken from the end of the earplug containing the tip cavity.
Figure 3:
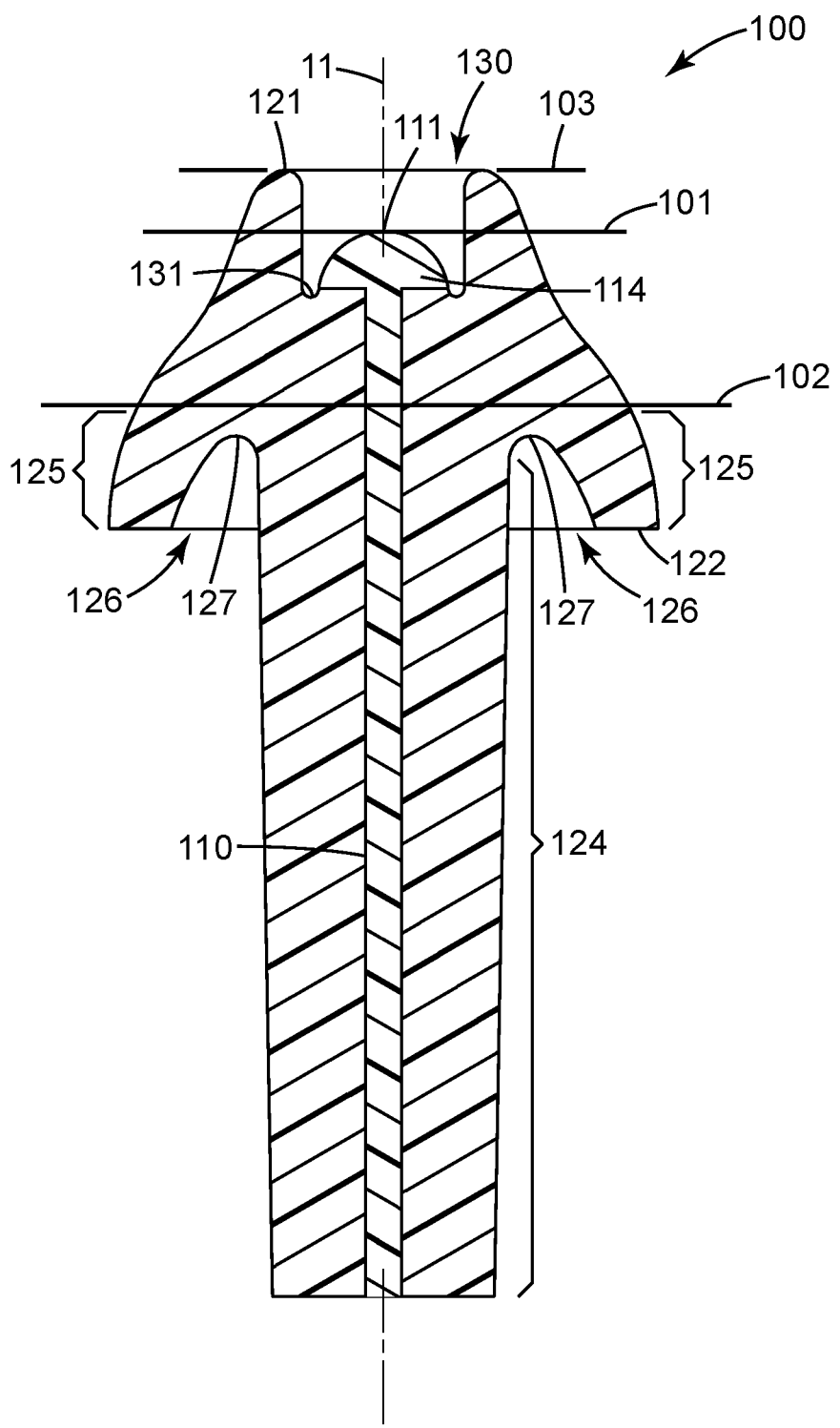
FIG. 3 is a cross-sectional view of the earplug of FIG. 1 and taken along line 3-3 in FIG. 2.

FIGS. 1-3 depict one illustrative embodiment of a push-to-fit earplug 100 as described herein. Earplug 100 includes an elongate core 110 made of a first material and having first and second ends 111 and 112 (respectively). Earplug 100 further includes an outer layer made of a second material and bonded, directly or indirectly, to at least a portion of outer major surface of elongate core 110. The outer layer of second material may, in one or more embodiments, be used to form a sound attenuating body 120 and may also be used to form an outer layer 125 of stem portion 124 extending from the sound attenuating body 120. In one or more embodiments, the core 110 may be described as extending through at least a portion of the sound attenuating body 120.

The sound attenuating body 120 is configured for at least partial insertion into the ear canal of a user to attenuate the passage of sound into the ear canal. Although not necessarily required, the stem portion 124 may, in one or more embodiments, have a smaller diameter than the sound attenuating body 120. During insertion of earplug 100 into the ear canal, stem portion 124 serves as a handle which may be gripped by a user. Earplug 100, and specifically sound attenuating body 120, is brought proximate to the user's ear and inserted into the ear canal. Sound attenuating body 120 compresses as it is positioned, and elongate core 110 provides sufficient stiffness to facilitate insertion. In use, sound attenuating body 120 is positioned substantially within an ear canal to block the passage of sound and stem portion 124 extends outwardly from the ear canal to provide a handle to remove the earplug.

In one or more embodiments of earplugs as described herein, such as earplug 110 depicted in FIGS. 1-3, the sound attenuating body 120 includes a tip 121 and a base 122. The tip 121 of the sound attenuating body 120 is located proximate the first end 111 of the core 110. The base 122 of the sound attenuating body 120 is located closer to the second end 112 of the core 110. The core 110 may, in one or more embodiments (such as that depicted in FIGS. 1-3), extend through at least a portion of the sound attenuating body 120.

Although not required, one or more embodiments of the earplugs as described herein may include a sound attenuating body 120 in which the base 122 of the sound attenuating body 120 is wider than the tip 121 of the sound attenuating body 120. Width, as used in this description, is measured in a dimension transverse to the longitudinal axis 11 that extends through the first end 111 and second end 112 of the core 110.

In one or more embodiments of the earplugs as described herein, the sound attenuating body 120 may include a flange 125 that extends from the base 122 towards the tip 121 of the sound attenuating body 120. The flange 125 may be formed by a flange cavity 126 formed in the sound attenuating body 120, with the flange cavity 126 having a bottom 127 located at the upper end of the flange cavity 126. In one or more embodiments, the sound attenuating body 120 may be described as including a flange cavity 126 extending from the base 122 of the sound attenuating body 120 towards the tip 121 of the sound attenuating body 120. In one or more embodiments, the flange cavity 126 may be described as opening downward towards the second end 112 of the core 110 or, alternatively, away from the tip 121 of the sound attenuating body 120. The flange 125 may be defined as that portion of the sound attenuating body 120 that is located below a plane oriented orthogonal to the longitudinal axis 11 and intersects at least a portion of the bottom 127 of the flange cavity 126. As a result, the flange 125 is essentially cantilevered from the sound attenuating body 120. Because the flange 125 is connected to the sound attenuating body 120 at only one end, the flange 125 may deflect inwardly as the earplug 100 is advanced into an ear canal and/or is resident therein. That deflection of the flange 125 may, in one or more embodiments, improve insertion and/or comfort of the earplug 100.

The sound attenuating bodies of the earplugs as described herein include a tip cavity 130 that extends from the tip 121 of the sound attenuating body 120 towards a bottom 131 that is located nearer to the base of the sound attenuating body 120. The tip cavity 130 may, in one or more embodiments, provide a volume into which the surrounding material of the sound attenuating body 120 can collapse as the earplug 100 is advanced into an ear canal and/or is resident therein.

Furthermore, the first end 111 of the core 110 is recessed into the tip cavity 130 which may, in one or more embodiments, reduce the likelihood that a user will feel the end 111 of the core as the sound attenuating body 120 is inserted into and/or resident within an ear canal. Although the first end 111 is recessed within the tip cavity 130, the first end 111 of the core 110 may extend into the tip cavity 130 such that the first end 111 of the core 110 is located above the bottom 131 of the tip cavity 130 (where "above" as used here means that the first end 111 is closer to the tip 121 of the sound attenuating body 120 than the bottom 131 of the tip cavity 130).

In addition to being characterized as extending into the tip cavity 130 such that it is located above the bottom 131 of the tip cavity, the first end 111 of the core 110 may, in one or more embodiments, be characterized as being recessed into the tip cavity 130 such that it is located below the tip 121 of the sound attenuating body 120. For example, the first end 111 of the core may be described as, in one or more embodiments, being located below the tip cavity opening plane 103. The tip cavity opening plane 103 is defined as a plane that is above and furthest from the first plane 101 that intersects with the sound attenuating body 120 around the entire perimeter of the tip cavity 130 (and is transverse to the longitudinal axis 11). As used in connection with the tip cavity opening plane 103, "above" means that the tip cavity opening plane 103 is located further from the bottom 131 of the tip cavity 130 than the first plane 101. In one or more embodiments, the first end 11 of the core 110 may be located 1 millimeter (mm) or more below the tip cavity opening plane 103.

In one or more embodiments, all or a portion of the first end 111 of the core 110 may be exposed within the tip cavity 130. In one or more alternative embodiments, the first end 111 of the core 110 may be partially or completely covered by a layer of the material used to form the sound attenuating body 120.

Although the illustrative embodiment of tip cavity 130 and a first end 111 of core 110 are depicted as having circular shapes (as seen in, e.g., FIG. 2), in one or more alternative embodiments, the tip cavities and/or first ends of the cores used in earplugs as described herein may have any suitable shape, e.g., hexagonal, pentagonal, octagonal, triangular, square, etc.

The tip cavities in the sound attenuating bodies of earplugs as described herein may be characterized in a variety of different manners. Referring to FIG. 3, the tip cavity 130 may be described as having a tip cavity cross-sectional area as measured in a first plane 101 that is located at the first end 111 of the core 110. The first plane 101 is oriented transverse to the longitudinal axis 11. Because the depicted embodiment of tip cavity 130 is circular it may also be described as having a diameter $D_{TC}$ as depicted in FIG. 2, which also, in essence, depicts the cross-sectional area of the tip cavity 130 as would be seen in first plane 101.

Further, the tip cavity cross-sectional area as seen in first plane 101 may be compared to the core cross-sectional area as measured in a second plane 102 that is located below the bottom 131 of the tip cavity 130 and above the base 122 of the sound attenuating body 120. As used herein, "below" means that the second plane 102 is located closer to the base 122 of the sound attenuating body 120 and the bottom 131 of the tip cavity 130. In one or more embodiments, the earplugs as described herein may be described as having a tip cavity cross-sectional area measured in the first plane 101 that is greater than core cross-sectional area measured in the second plane 102. In one or more embodiments, the tip cavity cross-sectional area may be 1.5 or more times the core cross-sectional area. In one or more alternative embodiments, the tip cavity cross-sectional area may be two (2) or more times the core cross-sectional area.

In one or more embodiments, the tip cavity cross-sectional area as measured in the first plane 101 located at the first end 111 of the core 110 may be in the range of from 5 $mm^2$ to 25 $mm^2$, e.g., approximately 12 $mm^2$. In one or more embodiments, the core cross-sectional area as measured in the second plane 102 located below the bottom 131 of the tip cavity 130 and above the base 122 of the sound attenuating body 120 may be in the range of from 1 $mm^2$ to 10 $mm^2$, e.g., approximately 5 $mm^2$.

In one or more embodiments, the core 110 may include a head 114, with the first end 111 of the core 110 located on the head. The head 114 may be described as being located in the tip cavity 130 at or above the bottom 131 of the tip cavity. The head 114 of the core 110 may, in one or more embodiments, be wider than the portion of the core 110 located between the head 114 and the second end 112 of the core 110 (with that portion of the core 110 being, in one or more embodiments, located below the bottom 131 of the tip cavity 130). In one or more embodiments, the head 114 may be formed of the first material making up the core 110 that is deformed during formation of the tip cavity 130.

In one or more embodiments, at least a portion of the head 114 may be described as having a head cross-sectional area that is equal to and/or greater than the core cross-sectional area. In the illustrative embodiment depicted in FIG. 3, the head 114 has a head cross-sectional area that is greater than the core cross-sectional area. The head cross-sectional area is measured in a plane that is orthogonal to the longitudinal axis 11, with the plane being located above the bottom 131 of the tip cavity 130 and below the first end 111 of the core 110 (i.e., below plane 101 as depicted in FIG. 3). The core cross-sectional area is, as described above, measured in a second plane 102 that is located below the bottom 131 of the tip cavity 130 and above the base 122 of the sound attenuating body 120.

In addition to having a first end 111 of the core 110 recessed within the tip cavity 130, the core 110 may also, in one or more embodiments, have a head 114 that has a non-planar upper surface that may also assist in reducing the likelihood that a user will feel the first end 111 of the core 110 as the sound attenuating body 120 is advanced into and/or resident within an ear canal. The upper surface of the head 114 is that surface of the head 114 that faces away from the bottom 131 of the tip cavity 130. The upper surface of the head 114 of the core 110 may, in one or more embodiments, have a semi-spherical shape as depicted in the illustrative embodiment seen in FIG. 3.

Another manner in which one or more embodiments of the sound attenuating bodies of earplugs as described herein may be characterized is by volume. The tip volume of a sound attenuating body 120 having a tip cavity as described herein may be defined as the volume of material of the sound attenuating body 120 that is located between the tip 121 of the sound attenuating body 120 and the first plane 101 which, as described above, is oriented transverse to the longitudinal axis 11 and is located at the first end 111 of the core 110. The tip cavity 130 of the sound attenuating body 120 may also be described as having a tip cavity volume that is defined as the volume of the tip cavity 130 between the first plane 101 and a tip cavity opening plane 103.

In one or more embodiments, the tip volume may be 0.02 cm$^3$ or more or, alternatively, 0.04 cm$^3$ or more. In one or more embodiments, the tip volume may be 0.2 cm$^3$ or less or, alternatively, 0.1 cm$^3$ or less. In one or more embodiments, the tip cavity volume may be 0.005 cm$^3$ or more or, alternatively, 0.01 cm$^3$ or more. In one or more embodiments, the tip cavity volume may be 0.04 cm$^3$ or less or, alternatively, 0.02 cm$^3$ or less.

Having defined the tip volume and the tip cavity volume of sound attenuating bodies in earplugs as described herein, the tip cavity volume of a tip cavity in one or more embodiments of a sound attenuating body as described herein may be less than, equal to, or even greater than the tip volume of the material surrounding tip cavity. The actual relationship between the tip cavity volume and the tip volume may, in one or more embodiments, be selected to provide benefits such as improved comfort during insertion of the earplugs into an ear canal and/or residence of the earplug in an ear canal. In one or more embodiments, the tip cavity volume may be 10% or more of the tip volume. In one or more alternative embodiments, the tip cavity volume may be 20% or more, or even 30% or more, of the tip volume. In one or more embodiments, the tip cavity volume may be 90% or less of the tip volume. In one or more alternative embodiments, the tip cavity volume may be 70% or less, or even 50% or less, of the tip volume.

The cores used in one or more embodiments of the earplugs as described herein may provide a substrate onto which an outer layer of material may be provided and, in one or more embodiments, may facilitate insertion of earplugs as described herein into the ear canal of a user. In the illustrative embodiment depicted in FIGS. 1-3, core 110 is made of a first material that exhibits greater rigidity or stiffness than a second material used to form the sound attenuating body 120 (and, in the depicted embodiment, an outer layer 125 of the stem portion 124), yet is soft enough to be comfortable and safe for a user. In one or more embodiments, the first material of the core 110 may be different than the material used to form the sound attenuating body 120 and the outer layer 125 of the stem portion 124. In one or more alternative embodiments, the first material of the core 110 may be the same material chemically, but that may be formed or provided in a manner that results in different stiffness between the first material and the second material (e.g., by virtue of density, hardness, etc.).

Including a core 110 in the stem portion 124 that is stiffer than the material forming the outer layer 125 of the stem portion 124 may, in one or more embodiments, provide a stem portion 124 having sufficient rigidity so that the earplugs described herein may be positioned for use at least partially in the ear of a user by pushing sound attenuating body 120 into the ear canal with an appropriate force. That is, a sufficiently stiff stem portion 124 may be provided by a core 110 and an outer layer 125 of the material used to form the sound attenuating body 120 so that earplug 100 may be positioned for use at least partially in the ear of a user without the need to first compress or "roll down" sound attenuating body 120. Direct insertion without the need to first compress or "roll down" sound attenuating body 120 may, for example, promote hygiene by limiting contact with sound attenuating body 120 prior to placement in the ear. In one or more embodiments, core 110 may also exhibit an appropriate level of flexibility such that it may slightly deform to follow the contours of the ear canal when positioned for use.

Elongate core 110 may, in one or more embodiments, be made from one or more materials that can suitably bond to, and are otherwise compatible with, the material used to form the sound attenuating body 120 and, in the depicted embodiment, the outer layer 125 of the stem portion 124. In one or more embodiments, core 110 may be made from a blend of polypropylene and styrene-ethylene-butylene-styrene (SEBS), such as TUFPRENE available from S&E Specialty Polymers, LLC. of Lunenburg, Mass. Other potentially suitable materials include SANTOPRENE 101-90, available from Exxon Mobile Corporation, and other materials exhibiting appropriate stiffness such that attenuating body 120 of earplug 100 may be easily inserted into the ear canal of a user.

Elongate core 110 may, in one or more embodiments, be made of one or more materials having a specified hardness. In various illustrative embodiments, the hardness of at least a portion of core 110 is between 50 and 100 Shore A, or between 70 and 90 Shore A, or about 80 Shore A. A desired hardness may depend on the dimensions of elongate core 110 such that elongate core 110 exhibits a desired stiffness.

In one or more illustrative embodiments, core 110 has a circular cross-section that is substantially uniform in size at any location between first end 111 and second end 112 such that elongate core 110 exhibits a generally cylindrical shape. A circular cross section may minimize edges that may cause discomfort by contacting portions of a user's ear. In one or more alternative embodiments, elongate cores used in earplugs as described herein may have a pentagonal, hexagonal, octagonal, triangular, square, or other suitable cross-section, and/or may have a cross-section size that varies along the length of earplug 100. In one or more embodiments, the outer major surface of cores used in earplugs as described herein may have a knurled, grooved, or otherwise textured surface. Such a surface may improve the ability of other materials to bond to the core. In one or more alternative embodiments, one or more intermediate layers may be provided between the core outer surface and the material used to form the sound attenuating bodies in the earplugs as described herein. Although the illustrative embodiment of core 110 includes only a single material, one or more alternative embodiments of cores used in earplugs as described herein may include multiple layers (which may or may not be concentric). For example, one or more layers may be used to provide a desired stiffness and one or more layers may be used to facilitate a robust bond with the outer layer, or to provide one or more other desired characteristics.

Figure 4:
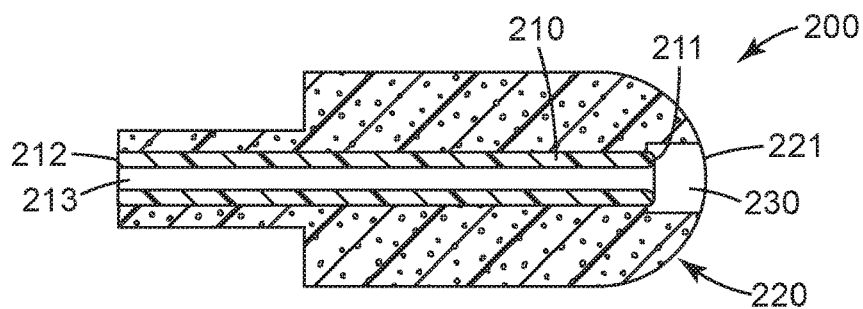
Figure 5:
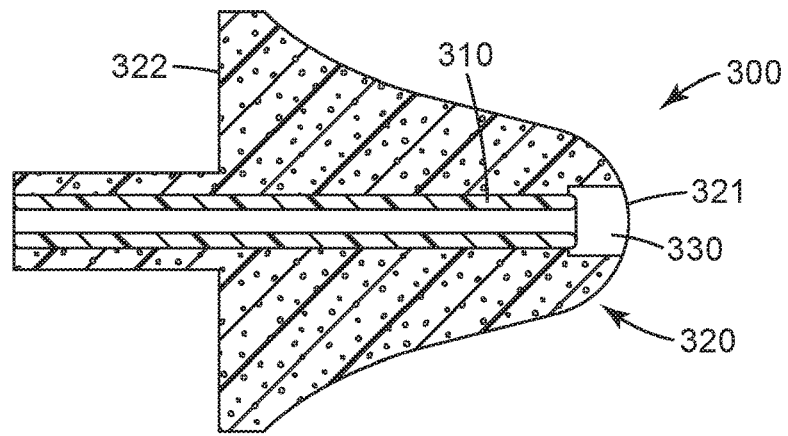
Figure 6:
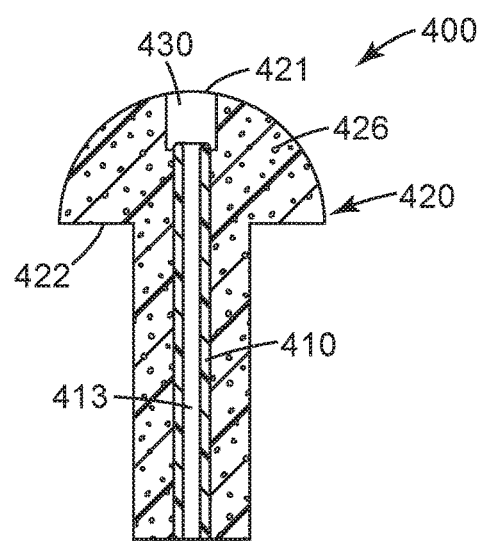

The specific shape of the sound attenuating body 120 as seen in the illustrative embodiment depicted in FIGS. 1-3 is only one example of a potentially suitable shape for an earplug as described herein. Examples of only a few of the myriad of alternative shapes that could be used for earplugs as described herein are depicted in FIGS. 4-6. With respect to the earplug 200 depicted in FIG. 4, the sound attenuating body 120 may be described as having a bullet shape and also includes a tip cavity 230 located at the tip 221 of the sound attenuating body 220 with the first end 211 of the core 210 recessed within the tip cavity 230.

Another variation depicted in connection with earplug 200 is that the core 210 includes a channel 213 that extends through the core 210 between the first end 211 and the second end 212 (where the core 110 of earplug 100 as depicted in FIGS. 1-3 is solid). Earplugs as described herein that include channels passing through the earplug may be manufactured such that components of a receiver or of a communication system may be attached to the earplug. Alternatively or in addition, a channel (such as, e.g., channel 213) may accommodate one or more filters or other passive hearing elements to provide an attenuation curve having a desired shape. For example, filters positioned in channel 213 may cause nonlinear attenuation of high level impulses produced by explosions, gunfire, or the like. Channels provided in one or more embodiments of earplugs as described herein may also provide a recess that a cord may be attached to, such that first and second earplugs may be joined, or that ends of a headband may be attached to in a semi-aural hearing protector.

Another illustrative embodiment of earplug 300 is seen in FIG. 5. Earplugs 300 include a sound attenuating body 320 having a tip 321 in which a tip cavity 330 is provided. A base 322 is located opposite the tip 321 of the sound attenuating body 320. The earplug 300 also includes a core 310 that extends through the sound attenuating body 320.

Still another illustrative embodiment of an earplug as described herein is depicted in FIG. 6 in which earplug 400 includes a sound attenuating body 420 having a tip 421 and a base 422. A tip cavity 430 is formed in the sound attenuating body 420. The earplug 400 also includes a core 410 which includes a channel 413.

The second material used to form the sound attenuating bodies of earplugs as described herein may, in one or more embodiments, be formed of a cellular material that includes a plurality of cells formed or contained within the material that makes up the sound attenuating bodies (and, in one or more embodiments, and outer layer of the stem portions of earplugs as described herein). Those cells contain a gas (such as, e.g., air) and may be formed by any suitable process, some examples of which are described herein. Referring to FIG. 6, one of the cells is identified by reference number 426.

In one or more embodiments, the gas cells formed in the sound attenuating bodies of earplugs as described herein may have a mean cell volume that can be related to the tip cavity volume as described herein with reference to FIG. 3. In one or more embodiments, the tip cavity volume may be described as being 20,000 or more times the mean cell volume. In one or more alternative embodiments the tip cavity volume may be described as being 45,000 or more times the mean cell volume.

The second material used to form the sound attenuating bodies and, in one or more embodiments, and outer layer of the stem portions of the earplugs as described herein may be a soft and pliable foam, rubber, polymer, or other suitable material that may be comfortably positioned in an ear canal of a user. In one or more illustrative embodiments, the second material may be an SEB S, such as MONPRENE MP1900 available from Teknor Apex of Pawtucket, R.I. Other suitable materials include plasticized polyvinyl chloride, ethylene propylene diene monomer (EPDM) rubber, styrene butadiene rubber (SBR), butyl rubber, natural rubbers, other thermoplastics, thermoset polymers, and other suitable materials as known in the art that can be formulated to exhibit an appropriate hardness range.

In one or more embodiments, the materials used to construct the cores and sound attenuating bodies may be selected such that the primary source of bonding between the core and material used for the sound attenuating body (directly or indirectly) is thermal bonding. In one or more embodiments, an additional adhesive is not required to bond the core to the sound attenuating body and, as a result, an adhesive is not present between core and the sound attenuating body. Although the sound attenuating bodies of earplugs as described herein may be described as being constructed of a second material, in one or more embodiments the sound attenuating bodies may be constructed of multiple layers of the same or different materials (which may be, e.g., arranged concentrically). For example, a first layer may be used to provide desired characteristics for contacting an ear canal of a user and a second layer may be used to facilitate a robust bond with the core, while one or more additional layers may be used to provide other desired characteristics.

The second material used in the sound attenuating bodies of earplugs as described herein may be selected to control the friability of the outer surface of the sound attenuating bodies such that it may not easily be broken or disintegrate during use. The friability of an earplug may be controlled in part by selecting a material having an appropriate molecular weight, with higher molecular weight generally resulting in a less friable earplug. In an exemplary embodiment, outer layer 142 includes an SEBS having a molecular weight between 100,000 Daltons and 200,000 Daltons, as measured by gel permeation chromatography analysis as known in the art, such as according to ASTM D6474-99.

The density of outer layer of second material used in the sound attenuating bodies as used in earplugs as described herein can, in one or more embodiments, be controlled during manufacturing to provide a specified density as desired for a particular application. The second material may, in one or more embodiments, exhibit a density that varies by thickness, for example, such that the second material used in the sound attenuating bodies has an integral outer skin that is more dense than the second material located closer to the core. Such a skin may be present on one or both of sound attenuating body and the stem portion (where the stem portion includes, for example, a layer of the second material used in the sound attenuating body). Alternatively, the second material used to construct the sound attenuating body and/or an outer layer of the stem portion may have a substantially uniform density.

In one or more embodiments in which the stem portion includes a layer of the second material used in the sound attenuating body and, irrespective of the presence of an integral outer skin or varying densities within sound attenuating body and/or the outer layer of stem portion, the second material of the sound attenuating body may have a first average density $\rho 1$ and the second material in the outer layer of the stem portion may have a second average density $\rho 2$. First and second average densities $\rho 1$ and $\rho 2$ can be found by averaging the densities at each location of sound attenuating body or outer layer of stem portion. Without being bound by theory, the average density is believed to provide an indication of the ability of sound attenuating body or outer layer of stem portion to compress or otherwise conform when subjected to an external force. The first average density $\rho 1$ of a sound attenuating body may, in one or more embodiments, be selected such that a sound attenuating body may provide a comfortable fit by conforming to the ear canal of a user, while providing a desired level of sound attenuation. In various illustrative embodiments, the first average density $\rho 1$ of the second material in a sound attenuating body, comprising a foamed SEBS for example, is between 100 kg/m$^3$ and 180 kg/m$^3$, or 110 kg/m$^3$ and 160 kg/m$^3$, or may be about 125 kg/m$^3$. The second average density $\rho 2$ of the second material in the outer layer of stem portion may be greater than the first average density $\rho 1$, and in various illustrative embodiments is between 200 kg/m$^3$ and 300 kg/m$^3$, 225 kg/m$^3$ and 275 kg/m$^3$, or may be about 250 kg/m$^3$. Accordingly, in various illustrative embodiments, the second average density $\rho 2$ of stem portion 124 of outer layer 120 is greater than 1.2, 1.5, 2 or more times the first average density $\rho 1$ of the second material of the sound attenuating body.

Figure 7:
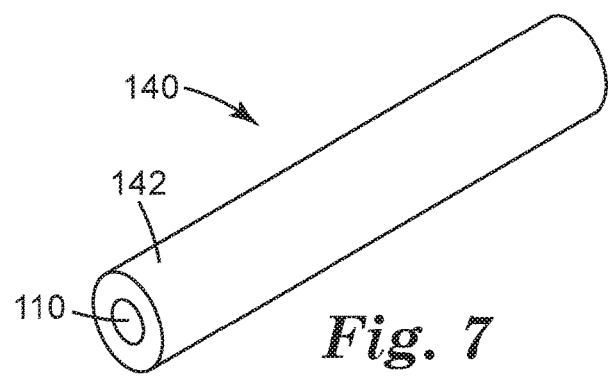
FIG. 7 is a perspective view of one illustrative embodiment of a pre-form that includes a core and an outer layer in an intermediate state of one illustrative embodiment of a method of making an earplug as described herein.

One or more embodiments of the earplugs as described herein may be formed in a multiple step process. In one or more embodiments, the earplugs described herein may be formed in a process that involves an intermediate state in which a core is covered with an outer layer of a second material (directly or indirectly), to result in a pre-formed hearing protection device that may be referred to as a pre-form, but which does not yet include a sound attenuating body. One illustrative embodiment of a pre-form is depicted in FIG. 7. The pre-form 140 includes an outer layer 142 located over a core 110. In one or more embodiments, the outer layer 142 of pre-form 140 includes an unactivated foaming agent. In one or more embodiments, the unactivated foaming agent includes an expandable sphere foaming agent that includes thermoplastic spheres, for example, that include a shell encapsulating a hydrocarbon or other appropriate gas that expands when exposed to heat or other activation source. Expansion of the thermoplastic shell results in an increased volume and reduced density of the material of outer layer 142. The unactivated foaming agent may also be a chemical foaming agent that includes an expandable material that is self-contained or otherwise not contained by an expandable sphere. Activation of such a foaming agent causes the expandable material to expand creating voids or gaps in the material of the outer layer.

In one or more embodiments, the outer layer 142 of pre-form 140 includes an unactivated expandable sphere foaming agent and an unactivated chemical foaming agent. Activation of the foaming agent or agents present in outer layer 142, and the associated expansion of outer layer 142, can be controlled to provide an earplug having a sound attenuating body and outer layer of stem portion exhibiting a desired shape, density, hardness, and other desired characteristics. The presence of both an expandable sphere foaming agent and a chemical foaming agent may assist in providing sufficient structure and expansion such that the outer layer may be appropriately formed during activation, while reducing the hardness of the outer layer from a level that would otherwise result if only an expandable sphere foaming agent were used. Some or all of a gas generated by a chemical foaming agent may escape during activation such that some or all of the gas is not present in the outer layer after activation. Some or all of an expandable sphere foaming agent may remain in the outer layer of a final earplug such that a final earplug may include thermoplastic spheres. In one or more illustrative embodiments, the material used in outer layer 142 which forms the sound attenuating bodies and an outer layer of the stem portions of earplugs as described herein may include between 1% and 5% weight, and may include approximately 3% weight, of the foaming agent or remnants of the foaming agent after being formed into the sound attenuating body and the outer layer of the stem portion.

In the intermediate state shown in FIG. 7, pre-form 140 may have a length that is roughly equivalent to the desired length of an earplug to be formed from the pre-form 140. In one or more alternative embodiments, the pre-form 140 may have an extended length that is sufficient for subsequent formation of two or more earplugs. Pre-form 140 having an extended length may facilitate handling for subsequent processing and activation of the foaming agent. In one or more embodiments, pre-form 140 is cut to an extended length that can be subsequently cut and activated to yield a desired quantity of earplugs. An extended pre-form 140 may be coiled or otherwise shaped for ease in transporting or handling.

Methods of making personal protective equipment, such as earplugs as described herein, may include covering a core with an outer layer, and applying heat to at least a portion of the outer layer such that at least a portion of the outer layer expands to form a sound attenuating body and, in one or more embodiments, an outer layer of a stem portion. Expansion of the outer layer may, in one or more embodiments, occur due to activation of a foaming agent present in the material of the outer layer and can be controlled by positioning at least a portion of the outer layer in a mold prior to expansion. Portions of the outer layer may be confined by the shape of the mold as the outer layer expands, or are shielded from heat to limit activation of the foaming agent.

Figure 8:
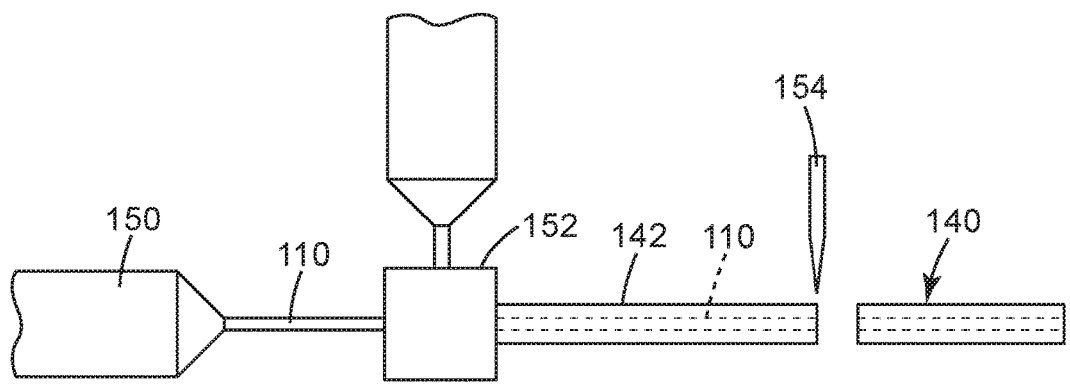
FIG. 8 is a schematic representation of one illustrative embodiment of a manufacturing process as described herein.

A schematic diagram of one illustrative embodiment of a process of making earplugs as described herein is depicted in FIG. 8. In the depicted process, an extended core 110 is formed by extruding a first material through a first die 150 and drawing the first material to an appropriate diameter. As described above, the core may be solid or may include a longitudinal channel extending through all or a portion of core 110, and may include one or more concentric layers having differing characteristics. The first material may be cooled such that it remains stable in subsequent steps of the manufacturing process. The magnitude of temperature change may depend on the materials used and the desired characteristics of the final product. In one or more embodiments, elongate core 110 is cooled as necessary such that it exhibits a temperature at a point before being covered by second die 152 that is lower than an activation or curing temperature of the second material used for outer layer 142. Prior to being covered by the second material of outer layer 142, elongate core 110 has an extended length and is not yet cut to the desired length for an earplug.

In the embodiment shown in FIG. 8, elongate core 110 is covered, directly or indirectly, with an outer layer 142 comprising a second material by second die 152. Second die 152 may be a co-extrusion die or other suitable die as known in the art. In one or more embodiments, the second material includes a thermoplastic and one or more unactivated foaming agents. Outer layer 142 is applied to elongate core 110 while remaining at a temperature below an activation temperature of the unactivated foaming agents. In one or more embodiments, the second material includes SEBS and a foaming agent having an activation temperature between 100° C. and 205° C., 120° C. and 190° C., or of about 170° C. Other suitable materials may include plasticized polyvinyl chloride, ethylene propylene diene monomer (EPDM) rubber, styrene butadiene rubber (SBR), butyl rubber, natural rubbers, other thermoplastics, thermoset polymers, and other suitable materials as known in the art. In embodiments in which outer layer 142 includes a second material having a rubber or thermoset polymer, outer layer 142 may be applied at a temperature below a vulcanizing or curing temperature of the rubber or thermoset polymer. In such an embodiment, outer layer 142 may include an unactivated foaming agent and an uncured or partially cured rubber or thermoset polymer that can be subsequently activated and cured, respectively, with heat or other suitable activation or curing process.

The weight percentage of foaming agent in outer layer 142 when initially applied to elongate core 110 may be selected based on the type of thermoplastic or other material used and the desired final shape, density, hardness or other characteristics of sound attenuating body of an earplug as described herein. In one or more embodiments, outer layer 142 has an initial composition of between 90% and 99.5% SEBS and between 10% and 0.5% of an appropriate unactivated foaming agent, or of approximately 93% SEBS and 7% of an unactivated expandable sphere foaming agent, such as EXPANCEL 930 DU 120, EXPANCEL 920 DU 120, both available from Eka Chemicals AB of Sundsvall, Sweden. In one or more alternative embodiments, outer layer 142 has an initial composition including an unactivated chemical foaming agent such as oxybis benzene sulfonyl hydrazide (OBSH) available from Biddle Sawyer Corp. of New York, N.Y. The presence of a chemical foaming agent such as an OBSH foaming agent may yield a sound attenuating body having a lower hardness value than a sound attenuating body formed of an outer layer including an expandable sphere foaming agent such as EXPANCEL as the only foaming agent. In one or more embodiments, outer layer 142 includes an unactivated expandable sphere foaming agent and an unactivated chemical foaming agent. The presence of both an expandable sphere foaming agent and a chemical foaming agent may assist in providing sufficient structure such that the outer layer may be appropriately formed and that may not be present with a chemical foaming agent alone, while reducing the hardness of the outer layer from a level that would otherwise result if only an expandable sphere foaming agent were used. Accordingly, the combination of a chemical foaming agent and an expandable sphere foaming agent may result in an outer layer having a hardness level appropriate for a desired application, such as for insertion into an ear canal. In one or more embodiments, outer layer 142 when initially applied may include between approximately 0.5% weight and 3% weight of an unactivated chemical foaming agent, or of approximately 2% weight of an unactivated chemical foaming agent, and between approximately 0.5% weight and 9.5% weight of an unactivated expandable sphere foaming agent, or of approximately 2% weight of an unactivated expandable sphere foaming agent. Outer layer 142 may also include other suitable foaming agents, or various combinations of EXPANCEL foaming agents, OBSH foaming agents, and other suitable foaming agents. Outer layer 142 may further include pigment to impart a desired color, antioxidants, UV stabilizers, and oils or waxes to aid in extrusion and mold release as known in the art.

In one or more embodiments, outer layer 142 is in a molten state when covered over core 110. As a result, molecules of outer layer 142 and core 110, or of one or more intermediate layers, are believed to diffuse into the material or surface of each other and a thermal bond is formed. When the materials or surfaces cool and solidify, outer layer 142 remains thermally bonded, directly or indirectly, to core 110. In one or more embodiments, significant chemical bonding is absent such that the primary source of bonding between core 110 and outer layer 142 is thermal bonding. In one or more alternative embodiments, outer layer 142 contacts core 110 or one or more intermediate layers when covered over core 110 but no significant bond is formed between outer layer 142 and core 110 or one or more intermediate layers. Upon activation and/or curing of outer layer 142, a thermal bond may be formed, directly or indirectly, between outer layer 142 and core 110.

In one or more embodiments, core 110 may be covered with outer layer 142, or one or more intermediate layers, by laminating, molding, spraying, dipping, or other suitable process as known in the art as an alternative or in addition to second die 250. Such steps may occur before or after core 110 is cut to a desired length. Regardless of the process used, the temperature of outer layer 142 should remain below the activation temperature of the foaming agent(s) such that the foaming agent(s) remain unactivated during the covering process. In the event that an uncured or partially cured material is included in outer layer 142, such as an EPDM rubber or thermoset polymer, the temperature of outer layer 142 should remain below the curing temperature of the material.

In one or more embodiments, core 110 covered by outer layer 142 is cut to the length of a desired earplug with cutter 154. The result is pre-form 140 having core 110 and outer layer 142 in which outer layer 142 includes an unactivated foaming agent that may be subsequently activated to create an earplug having a sound attenuating body and an outer layer of the stem portion formed by the outer layer 142 of the pre-form 140 (see, e.g., sound attenuating body 120 and stem portion 124 of earplug 100 depicted in FIGS. 1-3).

Cutter 154 may cut pre-form 140 to a desired length of an earplug as described herein, or to an extended length sufficient for subsequent formation of two or more earplugs. In one or more embodiments, pre-form 140 is cut to an extended length that can be subsequently cut and activated, or vice versa, to yield a desired quantity of earplugs. An extended pre-form 140 may be coiled or otherwise shaped for ease of handling or transportation.

In one or more embodiments, the unactivated foaming agent present in outer layer 142 includes thermoplastic spheres encapsulating a hydrocarbon or other expandable material. Application of an appropriate amount of heat causes the thermoplastic shell and hydrocarbon to expand. In one or more alternative embodiments, the foaming agent includes, alone or in combination with an expandable sphere foaming agent, an expandable material that is self-contained or not otherwise encapsulated, and that produces gas when exposed to heat or other activation source. If left unrestrained, activation of the foaming agent(s) creates cells in outer layer 142, ultimately increasing volume and decreasing density of outer layer 142. Expansion of outer layer 142 can be controlled by the thickness and composition of outer layer 142, selective application of heat, catalyst, or other activation source, and/or by placing at least a portion of pre-form 140 in a mold to limit expansion of outer layer 142 as the foaming agent is activated.

Figure 9:
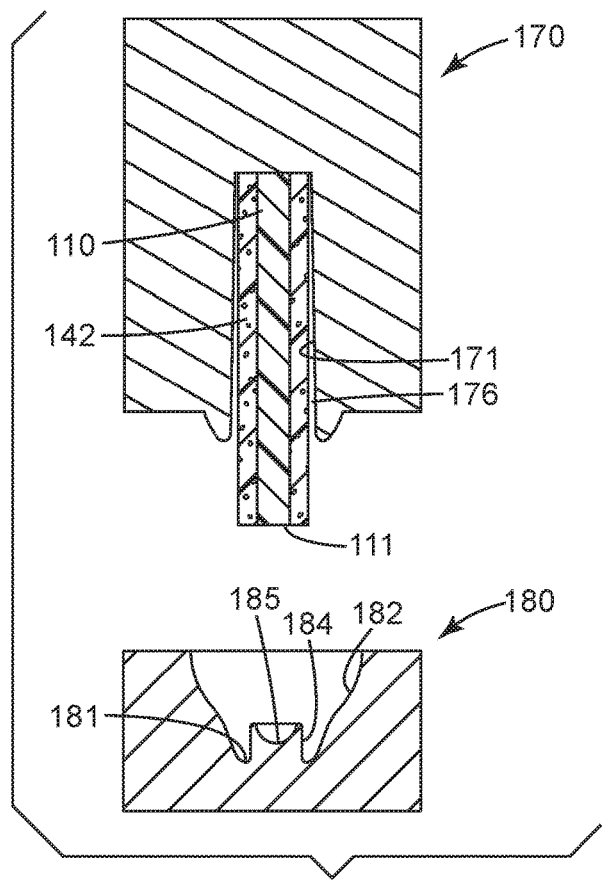
FIGS. 9 and 10 are cross-sectional views of one illustrative embodiment of a method of using a mold to manufacture an earplug as described herein.
Figure 10:
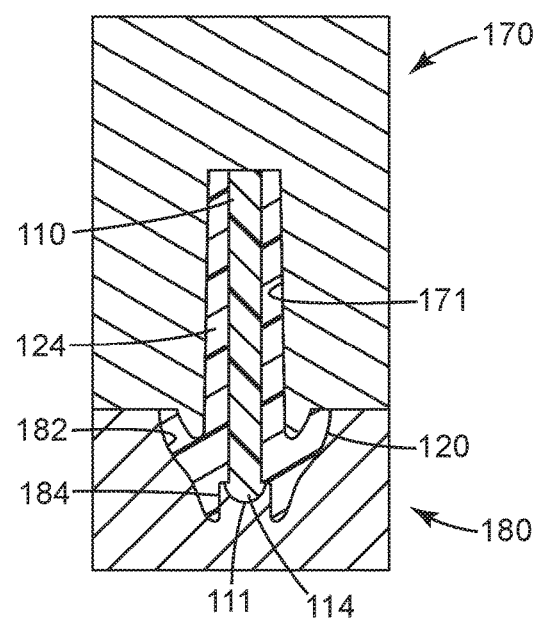

One illustrative embodiment of a mold assembly that may be used to manufacture one or more embodiments of earplugs as described herein is depicted in FIGS. 9 and 10. The mold assembly includes a stem portion 170 and a sound attenuating body portion 180. The stem portion 170 and the sound attenuating body portion 180 include, respectively, a stem cavity 171 and a sound attenuating body cavity 182. The stem cavity 171 and the sound attenuating body cavity 182 are used to control expansion of an outer layer of a pre-form that includes, in one or more embodiments, a core 110 and an outer layer 142. The stem cavity 171 is in the form of a stem portion that receives a portion of pre-form. The pre-forms used in mold assemblies such as the illustrative embodiment of a mold assembly as depicted in FIGS. 9 and 10, may, in one or more embodiments, be cut to the length of a desired earplug prior to being placed in the mold assembly.

Heat is applied to the pre-form located in the mold assembly to raise the temperature of outer layer 142 at least to an activation temperature of a foaming agent present in outer layer 142 and cause outer layer 142 to expand as shown in FIG. 10. In one or more embodiments, a gap 176 may exist between the outer layer 142 of the pre-form and the inner surface of the stem cavity 171. Upon application of heat or other suitable activation source, a portion of outer layer 142 expands to fill gap 176 and substantially conforms to the shape of the stem cavity 171. In one or more embodiments, the stem portion of an earplug positioned in stem cavity 171 may be effectively shielded from heat such that activation of the foaming agent is limited. Alternatively or in addition, stem cavity 171 constrains outer layer 142 and substantially inhibits expansion caused by activation of the foaming agent that would otherwise result in a greater volume and less dense outer layer over the portion of the core 110 in the stem cavity 170. Due to the constraint of the mold and/or limited activation of the foaming agent, the stem portion of an earplug (see, e.g., stem portion 124 in earplug 100 as depicted in FIGS. 1-3) may have a greater average density and/or a greater hardness than that of sound attenuating body portion of the same earplug.

The illustrative mold assembly as described herein includes a sound attenuating body cavity 182 that is used to provide the shape of a sound attenuating body of an earplug as described herein. When a portion of pre-form is initially placed in the sound attenuating body cavity 182, the portion of the pre-form in the sound attenuating body cavity 182 does not occupy all of the cavity 182. As the material in outer layer 142 is heated it may be softened and a foaming agent in the outer layer 142 is activated, causing the material of the outer layer to expand to fill the sound attenuating body cavity 182. In one or more embodiments, some of the material in the portion of the outer layer 142 located in the stem cavity 171 may flow into the sound attenuating body cavity 182. In one or more embodiments, the mold assembly may include one or more small gas vents to allow excess gas to escape while preventing passage of any molten material as the material in the outer layer 142 expands.

In one or more embodiments, the mold assembly may be oriented such that the stem cavity 171 is positioned above the sound attenuating body cavity 182. In such an orientation, any flow of material from the stem cavity 171 into the sound attenuating body cavity 182 during the expansion process may be enhanced. In one or more embodiments, such an orientation may facilitate the formation of an integral skin on sound attenuating body of an earplug formed using the mold assembly because cells or gaps formed during activation of the foaming agent may tend to move upward and away from a lower surface of the sound attenuating body cavity 182.

In addition to forming the outer shape of the sound attenuating body of an earplug as described herein, the sound attenuating body cavity 182 also includes a boss 184 that extends upward toward the opening of the sound attenuating body cavity 182, i.e., extends towards the stem cavity 171 of the mold assembly. The boss 184 can be described as extending upwards from a bottom 181 of the cavity 182. The boss 184 is used, in one or more embodiments, to form the tip cavities in sound attenuating bodies of earplugs as described herein. The boss 184 may, in one or more embodiments, include a depression 185 that is positioned to receive the end 111 of the core 110 of the pre-form and, in one or more embodiments, to deform that end 111 as part of the process of manufacturing in earplug as described herein. In one or more embodiments, the deformation of the end 111 of the core 110 may produce a head 114 as described herein. That deformation of the end 111 of the core 110 may be, in one or more embodiments, caused by the application of heat and/or pressure by the depression 185 of boss 184.

After expansion of the outer layer 142 such that the material occupies all of the stem cavity 171 and the sound attenuating body cavity 182, the earplug thus formed may be cooled and ejected from the mold assembly. The earplug thus formed includes a sound attenuating body 120 having the shape of the sound attenuating body cavity 182, and a stem portion 124 having the shape of stem cavity 171. Due to the constraint of stem cavity 171 and/or limited activation of the foaming agent in the area of stem cavity 171, the material in the outer layer of the stem portion 124 (formed from the outer layer 142 of the pre-form) may have a greater average density and/or hardness than the material forming the sound attenuating body 120.

In one or more embodiments of earplugs as described herein, the earplugs may be formed from pre-forms having a total length along a longitudinal axis of between approximately 15 mm and 40 mm, e.g., of about 25.5 mm. In one or more embodiments, the outer layer 142 of a pre-form may have an outer diameter of between approximately 2.5 mm and 7.5 mm, e.g., of about 5.5 mm. In one or more embodiments of the pre-forms, the core may have an outer diameter of between approximately 1.5 mm and 3.5 mm, e.g., of about 2.5 mm. in those embodiments in which the core has a channel formed therethrough, the channel may have a diameter of between approximately 1.0 mm and 2.0 mm, e.g., or of approximately 1.5 mm.

After activation of outer layer 142 of a pre-form as described above, and earplug thus manufactured may have a total length L measured along a longitudinal axis between the tip of the sound attenuating body 120 and the opposite end of the stem portion 124 of between approximately 15 mm and 40 mm, e.g., of approximately 25.5 mm. In one or more embodiments, sound attenuating body 120 of earplugs as described herein may have an outer diameter (measured transverse to a longitudinal axis of the earplug) at its widest point between approximately 8 mm and 16 mm, e.g., of approximately 12.5 mm. In one or more embodiments, the stem portion 124 may have a diameter (measured transverse to a longitudinal axis of the earplug) of between approximately 3 mm and 10 mm, e.g., of approximately 6.5 mm. In one or more embodiments, the core may have an outer diameter (measured transverse to a longitudinal axis of the earplug and below the bottom of the tip cavity) of between approximately 1.5 mm and 3.5 mm, e.g., of approximately 2.5 mm. If provided in the core, a channel may have a diameter (measured transverse to a longitudinal axis of the earplug) of between approximately 1.0 mm and 2.0 mm, e.g., of approximately 1.5 mm. The dimensions of pre-forms used to manufacture earplugs as described herein and the earplugs themselves can be varied based on the materials used to form the sound attenuating bodies and/or the cores.

Earplugs as described herein may be made by one or more of the methods described herein. In one or more alternative embodiments, earplugs as described herein may also be made according to variations of methods described herein and other methods. For example, an earplug as described herein may be made by covering a relatively stiffer elongate core with an outer layer as a foaming agent is activated, or covering a relatively stiffer elongate core with an outer layer that has been previously foamed. The foamed outer layer may be subsequently cut, compressed, densified, or otherwise shaped to form an outer layer having a stem portion and a sound attenuating body having a tip cavity located therein.

Although the illustrative embodiments of earplugs described herein include a sound attenuating body that is made of material that is also used and integrally formed with at least the outer layer of a stem portion, one or more alternative embodiments of the earplugs as described herein can be made by any suitable technique. In one or more alternative embodiments, an earplug as described herein could be manufactured in a plurality of pieces that are then assembled and/or attached to each other to form a complete earplug. For example, a sound attenuating body and a stem portion may be separately constructed and then assembled together and attached by any suitable technique or combination of attachments, e.g., welds (sonic, thermal, chemical, etc.), adhesive, an interference fit, mechanical connections (threaded connection, mechanical fasteners, etc.).

U.S. patent application Ser. No. 13/547,189, titled Method of Making an Earplug and filed on Jul. 12, 2012, describes methods of making personal protective equipment such as a push-to-fit earplug and materials used in those methods that may be used in part and/or with some modifications to manufacture earplugs as described herein.

The earplugs and methods of making earplugs as described herein may, in one or more embodiments, provide one or more benefits. In one or more embodiments, the earplugs described herein may be comfortably positioned in the ear canal of a user to provide a desired level of hearing protection, and the presence of a stiffer elongate core in the earplug may promote hygiene and/or reduce insertion time by eliminating the need to roll down a sound attenuating body prior to insertion. The presence of a tip cavity may, in one or more embodiments, allow one or more portions of a sound attenuating body surrounding the tip cavity to collapse inward upon insertion, thus possibly enhancing the ability of the earplugs described herein to conform to the ear canal of a user.

Illustrative embodiments of earplugs and methods of making earplugs as described herein are discussed and reference has been made to some possible variations. These and other variations and modifications in the invention will be apparent to those skilled in the art without departing from the scope of the invention, and it should be understood that this invention is not limited to the illustrative embodiments set forth herein. Accordingly, this invention is not limited to the above-described embodiments, but is to be controlled by the limitations set forth in the following claims and any equivalents thereof. This invention also may be suitably practiced in the absence of any element not specifically disclosed as necessary herein.

All patents and patent applications cited herein are incorporated by reference into this document in total. To the extent there is a conflict or discrepancy between this document and the disclosure in any such incorporated document, this document will control.

What is claimed is:

1. An earplug comprising:
   a solid core comprising a first end, a second end, and a major outer surface, wherein a longitudinal axis extends between the first end and the second end;
   a sound attenuating body attached to the major outer surface of the core, the sound attenuating body comprising a tip and a base, wherein the tip of the sound attenuating body is located proximate the first end of the core and the base is located closer to the second end of the core than the first end of the core, and wherein the core extends through at least a portion of the sound attenuating body; and
   a tip cavity in the sound attenuating body, wherein the tip cavity extends from the tip of the sound attenuating body towards a bottom nearest to the base of the sound attenuating body, the bottom of the tip cavity located between the tip and the base of the sound attenuating body, and wherein the tip cavity comprises a tip cavity cross-sectional area that is less than or equal to the solid core cross-sectional area, wherein the tip cavity cross-sectional area is measured in a first plane located at the first end of the core and transverse to the longitudinal axis, wherein the core cross-sectional area is measured in a second plane transverse to the longitudinal axis, wherein the second plane passes through the sound attenuating body below the bottom of the tip cavity and above the base of the sound attenuating body.

2. The earplug of claim 1, wherein the core is constructed of a first material and the sound attenuating body is constructed of a second material, wherein the first material is different than the second material.

3. The earplug of claim 2, wherein the first material comprises a thermoplastic.

4. The earplug of claim 2, wherein the second material comprises a thermoset polymer.

5. The earplug of claim 1, wherein at least a portion of the first end of the solid core is exposed at the bottom of the tip cavity.

6. The earplug of claim 1, wherein the first end of the solid core is located above the bottom of the tip cavity.

7. The earplug of claim 1, wherein the solid core comprises a head located in the tip cavity, wherein the first end of the solid core is located on the head, and wherein at least a portion of the head comprises a head cross-sectional area that is less than or equal to the solid core cross-sectional area, wherein the head cross-sectional area is measured in a plane orthogonal to the longitudinal axis and located above the bottom of the tip cavity and below the first end of the solid core.

8. The earplug of claim 1, wherein the solid core comprises a head located in the tip cavity, and wherein the head comprises a non-planar upper surface facing away from the bottom of the tip cavity.

9. The earplug of claim 1, wherein the solid core comprises a head located in the tip cavity, and wherein the head comprises a semispherical upper surface facing away from the bottom of the tip cavity shape.

10. The earplug of claim 1, wherein the sound attenuating body comprises a tip volume that is defined as a volume of material of the sound attenuating body located between the tip and the first plane, and wherein the tip cavity comprises a tip cavity volume that is defined as the volume of the tip cavity between the first plane and a tip cavity opening plane that is defined as the plane furthest from the first plane that is transverse to the longitudinal axis and that intersects with the sound attenuating body around the entire perimeter of the tip cavity.

11. The earplug of claim 1, wherein the sound attenuating body comprises a flange cavity extending from the base of the sound attenuating body towards the tip of the sound attenuating body, wherein the sound attenuating body comprises a cantilevered flange formed around the flange cavity and extending from the base of the sound attenuating body towards the tip of the sound attenuating body.

12. The earplug of claim 1, wherein the sound attenuating body is thermally bonded to at least a portion of the outer major surface of the solid core.

13. The earplug of claim 1, wherein an adhesive is not present between the outer major surface of the solid core and the sound attenuating body.

14. The earplug of claim 1, wherein the solid core comprises a cross-section that is uniform at any location between the bottom of the tip cavity and the second end of the solid core.

15. The earplug of claim 1, wherein the core comprises a channel extending through the core from the first end to the second end.

16. A method of making an earplug, the method comprising:
covering at least a portion of a major outer surface of a core that comprises a first material with a second material that comprises an unactivated foaming agent, wherein the core comprises a first end, a second end, and a major outer surface, wherein a longitudinal axis extends between the first end and the second end;
inserting the first end of the core and at least a portion of the second material into a mold cavity; and
activating the unactivated foaming agent in the mold cavity to form a sound attenuating body in the mold cavity that is attached to the major outer surface of the core, wherein the sound attenuating body comprises:
a tip and a base, wherein the tip of the sound attenuating body is located proximate the first end of the core and the base is located closer to the second end of the core than the first end of the core; and
a tip cavity in the sound attenuating body, wherein the tip cavity extends from the tip of the sound attenuating body towards a bottom nearest to the base of the sound attenuating body, the bottom of the tip cavity located between the tip and the base of the sound attenuating body, and wherein the tip cavity comprises a tip cavity cross-sectional area that is less than or equal to the core cross-sectional area, wherein the tip cavity cross-sectional area is measured in a first plane located at the first end of the core and transverse to the longitudinal axis, wherein the core cross-sectional area is measured in a second plane transverse to the longitudinal axis, wherein the second plane passes through the sound attenuating body below the bottom of the tip cavity and above the base of the sound attenuating body.

17. The method of claim 16, wherein a boss extends into the mold cavity, wherein the boss is positioned to contact the first end of the core when the first end of the core is inserted into the mold cavity.

18. The method of claim 17, wherein the method further comprises deforming the first end of the core using the boss.

19. The method of claim 16, wherein the method further comprises deforming the first end of the core in the mold cavity.

20. An earplug comprising:
a solid core comprising a first end, a second end, and a major outer surface, wherein a longitudinal axis extends between the first end and the second end;
a sound attenuating body attached to the major outer surface of the solid core, the sound attenuating body comprising a tip and a base, wherein the tip of the sound attenuating body is located proximate the first end of the solid core and the base is located closer to the second end of the solid core, and wherein the core extends through at least a portion of the sound attenuating body; and
a tip cavity in the sound attenuating body, wherein the tip cavity extends from the tip of the sound attenuating body towards a bottom nearest to the base of the sound attenuating body, the bottom of the tip cavity located between the tip and the base of the sound attenuating body, and wherein the tip cavity comprises a tip cavity cross-sectional area that is less than or equal to the solid core cross-sectional area, wherein the tip cavity cross-sectional area is measured in a first plane located at the first end of the solid core and transverse to the longitudinal axis, and wherein the solid core cross-sectional area is measured in a second plane transverse to the longitudinal axis, wherein the second plane passes through the sound attenuating body below the bottom of the tip cavity and above the base of the sound attenuating body;
wherein the solid core comprises a head located in the tip cavity, wherein the first end of the solid core is located on the head and above the bottom surface of the tip cavity, and wherein at least a portion of the head comprises a head cross-sectional area that is greater than or equal to the solid core cross-sectional area, wherein the head cross-sectional area is measured in a plane that is orthogonal to the longitudinal axis and located above the bottom of the tip cavity and below the first end of the solid core;
wherein the solid core is made of a first material and the sound attenuating body is made of a second material, wherein the first material and the second material are different.

21. The earplug of claim 20, wherein the sound attenuating body comprises a flange cavity extending from the base of the sound attenuating body towards the tip of the sound attenuating body, wherein the sound attenuating body comprises a cantilevered flange formed around the flange cavity and extending from the base of the sound attenuating body towards the tip of the sound attenuating body.

\* \* \* \* \*